(12) United States Patent
Lee

(10) Patent No.: US 7,253,247 B2
(45) Date of Patent: Aug. 7, 2007

(54) METHOD OF MAKING AROMATIC DIHYDROXY DIACID DIHALIDES AND PRECIPITATES RESULTING THEREFROM

(76) Inventor: Kiu-Seung Lee, 10941 Lansdowne Ct., Midlothian, VA (US) 23113

( * ) Notice: Subject to any disclaimer, the term of this patent is extended or adjusted under 35 U.S.C. 154(b) by 23 days.

(21) Appl. No.: 11/180,241

(22) Filed: Jul. 13, 2005

(65) Prior Publication Data

US 2007/0015903 A1    Jan. 18, 2007

(51) Int. Cl.
*C08G 64/00* (2006.01)
(52) U.S. Cl. .................. 528/196; 428/411.1; 428/412; 524/459; 524/461; 528/198
(58) Field of Classification Search ............. 428/411.1, 428/412; 524/459, 461; 528/196, 198
See application file for complete search history.

(56) References Cited

U.S. PATENT DOCUMENTS 3,515,695 A    6/1970  Loughran et al.

FOREIGN PATENT DOCUMENTS

GB    1 399 085    6/1975
JP    61012730    *   1/1986

OTHER PUBLICATIONS

Iso et al., "Efficient Synthesis of Resin-Bould a-TMSdiazoketones and Their Use in Solid-Phase Organic Synthesis", Tetrahedron 56 (2000) pp. 5353-5361.

* cited by examiner

*Primary Examiner*—Terressa Boykin

(57) ABSTRACT

A method of making an aromatic dihydroxy diacid dihalide comprises forming a solution of an aromatic dihydroxy diacid in a solvent, contacting the aromatic dihydroxy diacid solution with a halogenating agent; heating the solution under an inert atmosphere to convert from 50 and 100 percent of the aromatic dihydroxy diacid to aromatic dihydroxy diacid dihalide, wherein the time required for the conversion is less than 4 hours, and removing at least a portion of the solvent.

10 Claims, No Drawings

METHOD OF MAKING AROMATIC DIHYDROXY DIACID DIHALIDES AND PRECIPITATES RESULTING THEREFROM

BACKGROUND OF THE INVENTION

1. Field of the Invention

This invention is directed to a method for synthesizing aromatic dihydroxy diacid dihalides and to precipitates made from such method.

2. Description of Related Art

Conversion of aromatic dihydroxy diacids into isolatable aromatic dihydroxy diacid dihalides has required the use of a solvent in the prior art. Otherwise a hydroxyl group on an aromatic ring would allow the compound to self-polymerize.

U.S. Pat. No. 3,515,695 discloses use of an aliphatic ether as a reaction medium to prepare 2,5-dihydroxyterephthaloyl chloride from its dicarboxylic acid. Aromatic dihydroxy diacids, however, have limited solubility in aliphatic ethers and require extended periods of heating to achieve conversion to the dihydroxy diacid dihalide.

U.S. Pat. No. 3,515,695 discloses heating for 24 hours to achieve conversion of 2,5-dihydroxyterephthalic acid to 2,5-dihydroxyterephthaloyl chloride.

A need is present for a new method for synthesizing aromatic dihydroxy diacid halides and precipitates.

SUMMARY OF THE INVENTION

This invention relates to a method of making an aromatic dihydroxy diacid dihalide, comprising the steps of:
a) forming a solution of an aromatic dihydroxy diacid in a solvent with the proviso that the aromatic dihydroxy diacid dihalide formed in step (c) is soluble in the solvent;
b) contacting the aromatic dihydroxy diacid solution with a halogenating agent;
c) heating the solution under an inert atmosphere to convert from 50 to 100 percent of the aromatic dihydroxy diacid to aromatic dihydroxy diacid dihalide, wherein the time required for the conversion is less than 4 hours; and
d) removing at least a portion of the solvent.

Upon removal of at least a portion of the solvent a precipitate is formed comprising 99 to 75 weight percent of aromatic dihydroxy diacid dihalide and 1 to 25 weight percent solvent, based on the weight of these two components.

DETAILED DESCRIPTION OF THE INVENTION

The aromatic dihydroxy diacid dihalide resulting from method steps (a), (b), (c) and (d) set forth in the Summary of The Invention is of the structure:

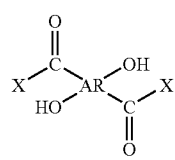 (a)

where AR represents a wholly aromatic ring system. Preferably, AR is a naphthalenic or more preferably a benzoic group shown by structures (b) and (c) respectively.

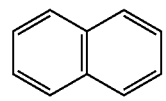 (b)

 (c)

Preferably, carboxylic acid halide groups (—CXO) are ortho to a hydroxyl group (—OH). Each X can be independently fluorine, chlorine, bromine, or iodine. Preferably, each X is independently chlorine or bromine.

Preferred aromatic dihydroxy diacid dihalides are 1,5-dihydroxy-2,6-naphthaloyl (di)chloride, 2,6-dihydroxy-1,5-naphthaloyl (di)chloride or 2,5 dihydroxyterephthaloyl (di) chloride or mixtures thereof which are shown below by structures (d)-(f) respectively. The aromatic dihydroxy diacid dihalide that is most preferred is 2,5 dihydroxyterephthaloyl (di)chloride.

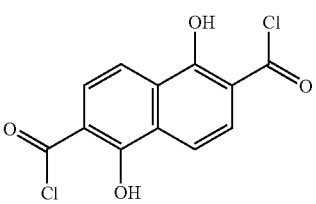 (d)

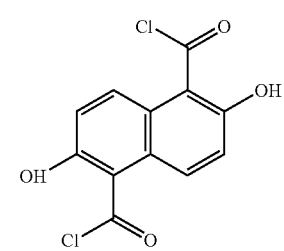 (e)

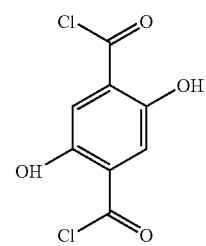 (f)

Method step (a) of the present invention comprises forming a solution of an aromatic dihydroxy diacid in a solvent. The aromatic dihydroxy diacid is of the structure:

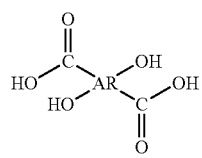

(g)

where AR is as defined previously, and the carboxylic acid groups preferably are each ortho to a distinct hydroxyl group. Preferably, AR is a naphthalenic or benzoic group, wherein the benzoic group is the most preferred aromatic ring system.

The preferred aromatic dihydroxy diacids are 1,5-dihydroxy-2,6-naphthalene dicarboxylic acid, 2,6-dihydroxy-1,5-naphthalene dicarboxylic acid or 2,5 dihydroxyterephthalic acid which are shown below as structures (h)-(j). The most preferred benzoic aromatic dihydroxy diacid is 2,5-dihydroxyterephthalic acid.

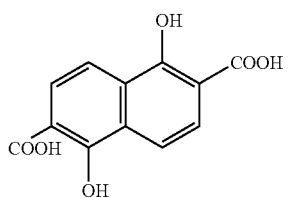

(h)

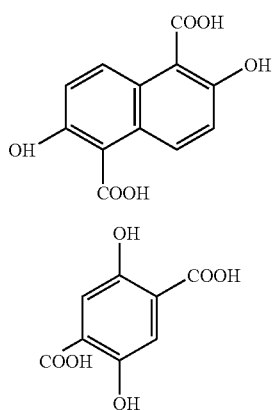

(i)

(j)

Suitable solvents for method step (a) include cyclic ether, such as tetrahydrofuran, tetrahydropyran, and mixtures thereof. The dihydroxy diacid is typically added to the solvent with mechanical stirring under an inert atmosphere substantially unreactive with the solvent, aromatic dihydroxy diacid, or other reagents. Suitable inert atmospheres include but are not limited to nitrogen, helium, and noble gases.

Preferably, the concentration of the dihydroxy diacid solution is in the range of 0.05 to 1 mole of diacid per liter of solution. More preferably, the concentration of the resulting dihydroxy diacid solution is in the range of about 0.1 to 0.5 mole of diacid per liter of solution. The addition of the dihydroxy diacid can be performed at a temperature at which the solvent is a liquid. In most cases the temperature is in a range from −5 to 65 degrees Celsius.

Method step (b) comprises contacting the aromatic dihydroxy diacid solution with a halogenating agent. The term "halogenating agent" means a material which reacts with the aromatic dihydroxy diacid to convert the aromatic dihydroxy diacid to the aromatic dihydroxy diacid dihalide. Typical halogenating agents include but are not limited to thionyl chloride, thionyl bromide, phosgene, chlorine, bromine and mixtures thereof. The preferred halogenating agent is thionyl chloride.

The halogenating agent can be added to the solution of the dihydroxy diacid under an inert atmosphere. The halogenating agent can optionally be dissolved in a solvent prior to addition to the dihydroxy diacid solution. Preferably, the optional solvent is the same solvent used in the forming step. If an optional solvent for the halogenating agent is used the solvent should desirably not render the dihydroxy diacid or dihydroxy diacid dihalide insoluble in the combined solvents.

Halogenating agents and dihydroxy diacid dihalides are highly reactive compounds and, their exposure to water can cause undesirable reactions to occur. Therefore, they can be reacted in an environment to minimize exposure to moisture. For example, if the halogenating agent is a liquid, the liquid can be added to the aromatic diacid solution under a dry inert atmosphere such as nitrogen gas. If the halogenating agent is a gas, it can contact the aromatic diacid solution under a substantially inert and low moisture atmosphere to avoid unwanted reactions. Preferably, the halogenating agent is a liquid. Preferably, the halogenating agent is present in a stoichiometric excess based on the amount needed to convert 100 percent of the aromatic dihydroxy diacid to aromatic dihydroxy diacid dihalide.

Step (c) of the method comprises heating the solution of step (b) under an inert atmosphere to convert 50 to 100 percent of the aromatic dihydroxy diacid to aromatic dihydroxy diacid dihalide. The time required for conversion of the aromatic dihydroxy diacid to the aromatic dihydroxy diacid dihalide is less than four hours, preferably, less than two hours, and most preferably, less than one hour. It is believed that a reaction time of at least three minutes is needed in many cases. The solution can be heated to a temperature near the boiling point of the solvent while the solution is stirred mechanically.

Step (d) of the method is the removal of at least a portion of the solvent from the reaction mixture. The reaction mixture can be heated under reduced pressure to remove the solvent by evaporation. Preferably, the removal of the solvent is performed under an inert atmosphere such as nitrogen to limit the ability of the aromatic dihydroxy diacid dihalide to self-polymerize.

Step (d) in removal of all or a portion of the solvent results in formation of a precipitate including the aromatic dihydroxy diacid dihalide as well as undesired compounds to the aromatic dihydroxy diacid dihalide. The undesired compounds can include but are not limited to, unhalogenated aromatic dihydroxy diacid, and mono-halogenated aromatic dihydroxy diacid monohalide, halogenating agent and reacted halogenating agent byproduct.

A more purified form of the aromatic dihydroxy diacid dihalide can be obtained by preferentially dissolving the dihalide in a further solvent. The solvent is chosen such that at least a portion of the undesired materials resulting from step (c) do not dissolve. The temperature is preferentially maintained at a temperature below which the aromatic dihydroxy diacid dihalide will self-polymerize. In most cases the temperature is maintained in the range of 25 to 65 degrees Celsius. Preferably, this temperature is below about 60 degrees Celsius. Insoluble undesired compounds can then be removed for example by filtration. Soluble undesired compounds can then be removed for example by recrystallization. Typical solvents include but are not limited to aliphatic hydrocarbons. Preferably, the solvent includes hexanes, heptanes or mixtures thereof. More preferably, the solvent contains a hexane.

The dihydroxy diacid dihalide can be recovered from the solvent by techniques such as recrystallization, evaporation of the solvent, or fractional distillation. Preferably, the solution of aromatic dihydroxy diacid dihalide in the solvent is cooled to cause the aromatic dihydroxy diacid dihalide to precipitate. A vessel containing the solution is typically cooled in an ice/water bath. The precipitate of aromatic dihydroxy diacid dihalide can then be isolated by for example filtration.

A precipitate resulting from method step (d) or from a further step can contain 75 to 99 weight percent of an aromatic dihydroxy diacid dihalide, and 1 to 25 weight percent of solvent based on the total weight of the solvent and aromatic diacid dihalide.

The inventors have found that if during purification a residual amount of second solvent is allowed to remain in the isolated solid of aromatic dihydroxy diacid dihalide any self-polymerization when stored at 25 degrees Celsius under Nitrogen is substantially reduced or eliminated. Typically the self-polymerization is less than 1 mole percent of the aromatic dihydroxy diacid dihalide per week. Preferably the self-polymerization is less than 1 mole percent of the aromatic dihydroxy diacid dihalide per month. In most cases a residual second solvent concentration is in a range of 1 to 25 weight percent of the total weight of recovered material. Preferably, the amount of residual second solvent is in the range of 15 to 25 weight percent of the total weight of recovered material. Dihydroxy diacid dihalides produced and isolated in this form allows for extended shelf life.

The dihydroxy diacid dihalides produced by this invention are useful as chemical intermediates in the areas of agricultural, medicinal, and polymer chemistry.

In the following examples all parts and percentages are by weight and degrees in centigrade unless otherwise indicated.

EXAMPLE

A solution was formed by dissolving 25.0 grams (0.126 mol) of 2,5-dihydroxyterephthalic acid in a solvent of 1250 ml of anhydrous tetrahydrofuran at room temperature. To this solution was added 45 grams (0.378 mol) of a halogenating agent, thionyl chloride. The mixture was heated to reflux using a heating mantle (65 degrees Celsius) for 2 hours under a nitrogen atmosphere. The tetrahydrofuran was removed under reduced pressure to form a precipitate.

To the precipitate was added 1500 ml of anhydrous hexane. The resulting mixture was heated to 60 degrees Celsius for 1 hour under a nitrogen atmosphere and filtered to remove insoluble undesired materials. The hexane solution was then allowed to cool to room temperature. Following this the solution was cooled in an ice/water bath. A precipitate was collected by filtration and placed in a vacuum dessicator at room temperature under reduced pressure for 15 hours.

The precipitate was then placed in a vacuum oven, which had been purged with nitrogen and the precipitate dried under reduced pressure. The oven temperature was maintained at 60 degrees Celsius for 16 hours. An orange/yellow solid product resulted from the drying step.

The orange/yellow solid was analyzed by NMR and found to contain 77.5 weight percent 2,5-dihydroxy-terephthaloyl dichloride and 22.5 weight percent hexanes.

What is claimed is:

1. A method of making an aromatic dihydroxy diacid dihalide, comprising:
    a) forming a solution of an aromatic dihydroxy diacid in a cyclic ether solvent with the provisio that the dihydroxy diacid dichloride formed in step (c) is soluble in the solvent;
    b) contacting the aromatic dihydroxy diacid solution with a halogenating agent;
    c) heating the solution under an inert atmosphere to convert from 50 to 100 weight percent of the aromatic dihydroxy diacid to aromatic dihydroxy diacid dihalide wherein the time for the conversion is less than 4 hours, and
    d) removing at least a portion of the cyclic ether solvent.

2. The method of claim 1 wherein the aromatic dihydroxy diacid is selected from the group consisting of 2,5-dihydroxy-terephthalic acid, 1,5-dihydroxy-2,6-naphthalene dicarboxylic acid, 2,6-dihydroxy-1,5-naphthalene dicarboxylic acid, and mixtures thereof.

3. The method of claim 2, wherein the solvent comprises tetrahydrofuran, tetrahydropyran, or mixtures thereof.

4. The method of claim 1, wherein the halogenating agent is selected from the group consisting of thionyl chloride, thionyl bromide, phosgene, chlorine, bromine and mixtures thereof.

5. The method of claim 1, wherein the halogenating agent is present in a stoichiometric excess based on the amount needed to convert 100 percent of the aromatic diacid to aromatic dihydroxy diacid dihalide.

6. The method of claim 1 comprising the further steps:
    e) combining dihydroxy diacid dihalide resulting from step (c) with a further solvent for the dihalide which does not dissolve at least a portion of the remaining components;
    f) recovering dihydroxy diacid dihalide from the solvent of step (e).

7. The method of claim 6, wherein the dihydroxy diacid dihalide is recovered as a solid from the solvent solution of step (e).

8. The method of claim 6 wherein the solvent of step (e) is selected from the group consisting of hexane, heptane, and mixtures thereof.

9. A purified aromatic dihydroxy diacid dihalide composition containing 1 to 25 weight percent aliphatic solvent when stored at about 25 degrees Celsius under Nitrogen atmosphere for 168 hours results in less than 1 percent of the aromatic dihydroxy diacid dihalide self polymerizing.

10. The purified dihydroxy diacid dihalide composition on claim 9 wherein the solvent comprises hexane or heptane.

* * * * *